United States Patent
Bachmaier et al.

(10) Patent No.: US 12,343,007 B2
(45) Date of Patent: Jul. 1, 2025

(54) KNOTLESS TISSUE REPAIR

(71) Applicant: Arthrex, Inc., Naples, FL (US)

(72) Inventors: Samuel Bachmaier, Mauern (DE);
Jeremy B. Stephens, Naples, FL (US);
John P. Gualdoni, Naples, FL (US);
Jacob A. Jolly, Naples, FL (US);
Justin M. Boyle, Naples, FL (US);
Andrew K. Osika, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1026 days.

(21) Appl. No.: 17/271,506

(22) PCT Filed: Aug. 30, 2019

(86) PCT No.: PCT/US2019/049096
§ 371 (c)(1),
(2) Date: Feb. 25, 2021

(87) PCT Pub. No.: WO2020/047431
PCT Pub. Date: Mar. 5, 2020

(65) Prior Publication Data
US 2021/0196264 A1    Jul. 1, 2021

Related U.S. Application Data (60) Provisional application No. 62/725,328, filed on Aug. 31, 2018.

(51) Int. Cl.
*A61B 17/06*    (2006.01)
(52) U.S. Cl.
CPC .............................. *A61B 17/06166* (2013.01)

(58) Field of Classification Search
CPC . A61B 17/04; A61B 17/0401; A61B 17/0485; A61B 17/06166; A61B 2017/0477; A61B 2017/06185
See application file for complete search history.

(56) References Cited

U.S. PATENT DOCUMENTS

| | | |
|---|---|---|
| 7,153,312 B1 | 12/2006 | Torrie et al. |
| 9,545,251 B2 | 1/2017 | Bojarski et al. |
| 9,861,354 B2 | 1/2018 | Saliman et al. |
| 9,924,939 B1 | 3/2018 | Anderson |
| 2010/0130990 A1 | 5/2010 | Saliman |
| 2010/0249809 A1 | 9/2010 | Singhatat et al. |
| 2013/0096612 A1 | 4/2013 | Zajac et al. |
| 2014/0052179 A1 | 2/2014 | Dreyfuss et al. |
| 2016/0302789 A1* | 10/2016 | Hirotsuka .......... A61B 17/0469 |
| 2017/0128061 A1 | 5/2017 | Stone et al. |
| 2018/0221133 A1* | 8/2018 | Lund .................. A61B 17/0401 |
| 2018/0360437 A1 | 12/2018 | Sengun et al. |
| 2019/0038276 A1* | 2/2019 | Jackson ................ A61F 2/0811 |

FOREIGN PATENT DOCUMENTS

| | | |
|---|---|---|
| CA | 2846244 C | 4/2018 |
| EP | 2 698 117 A1 | 2/2014 |
| JP | 2013-233434 A | 11/2013 |
| JP | 2014-61380 A | 4/2014 |
| JP | 2016-507346 A | 3/2016 |
| WO | WO 2014/134102 A2 | 9/2014 |
| WO | WO 2017/189096 A1 | 11/2017 |

\* cited by examiner

*Primary Examiner* — Diane D Yabut
*Assistant Examiner* — Christian D. Knauss
(74) *Attorney, Agent, or Firm* — Blank Rome LLP (57) ABSTRACT

Surgical constructs and methods for closing a tear in soft tissue without knot tying and without the use of fixation devices are disclosed.

6 Claims, 10 Drawing Sheets

KNOTLESS TISSUE REPAIR

RELATED APPLICATION

This application claims priority to U.S. Provisional Application Ser. No. 62/725,328, filed Aug. 31, 2018, the entire disclosure of which is herein incorporated by reference.

BACKGROUND

This disclosure relates to a knotless surgical construct for repairing damaged soft tissue and a method for repairing the tissue using the same. Surgical procedures are often performed to repair musculoskeletal injuries, such as those sustained during sporting activities. Tears in the meniscus can be repaired by deploying implants on either side of the tear, tensioning suture between the implants to close the tear, and allowing it to heal.

SUMMARY

This disclosure relates to a knotless surgical construct that comprises, inter alia, at least one flexible strand comprising a free end, a loop end opposite the free end, and a repair length therebetween, the repair length may be configured to form a continuous and adjustable repair loop when the free end extends through the loop end, the repair loop may be configured to encircle a tear in tissue; and a self-locking device is located adjacent to the loop end of the flexible strand, the self-locking device may be configured to fix the repair loop once the repair loop is tensioned around the tear without the use of a knot, a fixation device, or an implant.

The free end of the flexible strand may extend through the self-locking device; the self-locking device can be a finger-trap suture; and/or the finger-trap suture may be integral with the flexible strand. The repair length may double on itself to define a cinch loop that extends through the loop end such that the repair loop comprises at least two flexible strand lengths. A separate shuttling device can be coupled to the free end of the flexible strand. The shuttling device can be a shuttle suture. The flexible strand may be a suture, for example.

A method includes, inter alia, passing, in a first direction, a free end of at least one flexible strand of a surgical construct through or around tissue that is damaged; threading the free end through a loop end of the flexible strand that is opposite the free end, thereby forming a continuous and adjustable repair loop with a repair length of the flexible strand that is between the free end and the loop end, such that the repair loop encircles a tear in the tissue; pulling on the free end to tension the repair loop around the tear in the damaged tissue; and after the step of pulling on the free end to tension the repair loop, fixing the repair loop without knotting or anchoring the flexible strand to secure the repair.

The free end of the flexible strand and the loop end of the flexible strand may extend from inferior and superior surfaces, respectively, of the tissue. The tissue that is damage is a meniscus and the superior and inferior surfaces are femoral and tibial surfaces, respectively. The flexible strand self-locks when fixing the repair loop. The flexible strand self-locks using a finger-trap suture that is adjacent the loop end of the flexible strand. The free end of the flexible strand extends through the finger-trap suture.

A method may include passing the free end, in a second direction, through or around the tissue, the second direction being the reverse of the first direction, so that the repair loop doubles to comprise at least two flexible strand repair lengths. Passing the free end in the second direction through or around the tissue is before the step of pulling on the free end of the flexible strand to tension the repair loop. Passing the free end in the second direction includes passing the free end through the loop end for a second time, thereby forming a cinch loop coupled to the loop end. Passing the free end of the flexible strand through or around tissue that is damaged includes wrapping the repair length of the flexible strand around an outside of the tissue to form the repair loop.

The tissue may be, for example, a meniscus, and the repair loop encircles the outside of the meniscus. Passing the free end of the flexible strand through or around tissue that is damaged includes passing at least a portion of the repair length of the flexible strand through a thickness of the tissue that is damaged near the tear. The tissue may be a meniscus and the repair loop extends through the thickness of the meniscus. At least another portion of the repair length of the flexible strand may extend through the thickness of the tissue at a location different than the at least a portion of the repair length. The tissue may also be a capsular, a labrum, or the like.

The disclosure relates to a knotless surgical construct for tissue repair that comprises, inter alia, a flexible strand that comprises opposite first and second free ends, and a repair length therebetween, the repair length may be configured to form first and second adjustable closed loops via first and second splice regions, respectively, in the repair length. A passer may be loaded onto the flexible strand to facilitate passing the flexible strand through the tissue. The flexible strand is devoid of any fixation devices such that the first and second adjustable loops may be tensionable by the first and second free ends, respectively, to close the tear in the tissue without the use of any knots or fixation devices.

A flexible strand may be a single strand, such as a single suture.

First and second adjustable closed loops may be interlinked with one another at loop ends, respectively, to form a doubled repair loop that is adjustable to close the tear in the tissue. First and second adjustable closed loops may be interlinked at a location generally opposite from the first and second splice regions.

First and second splice regions may be located adjacent one another. First and second splice regions may be spaced from one another by less than 6 mm.

Each of the first and second splice regions may have a shortened length, and the shortened length can be, for example, about 3 to about 6 mm.

A passer may be coupled to one of the first and second adjustable loops.

The disclosure also includes a method of knotless tissue repair comprising, inter alia, threading a first free end of a flexible strand of a knotless surgical construct through a first splice region in the flexible strand to create a first adjustable closed loop; passing the first adjustable closed loop through a tear in the tissue such that a loop end thereof is located at one side of the tear in the tissue and the first splice region is located at the other side of the tear; thereafter passing a second free end of the flexible strand through the loop end of the first adjustable closed loop and threading the second free end through a second splice region in the flexible strand to create a second adjustable closed loop that is interlinked with the first adjustable closed loop such that the first and second adjustable closed loops form a doubled repair loop that is adjustable; and pulling the first and second free ends of the flexible strand to decrease the perimeters of the first and second adjustable closed loops, respectively, and thereby decreasing the perimeter of the doubled repair loop until the tear in the tissue is closed without the use of knots or fixation devices.

A passer may be coupled to the loop end of the first adjustable closed loop to pass the same through the tear in the tissue in the method. The passer may be removed after the first adjustable close loop is passed through the tear in the tissue.

A passer may be coupled to the second free end of the flexible strand to pass the second free end through the loop end of the first adjustable closed loop.

In a method, before pulling the first and second free ends of the flexible strand to decrease the perimeters of the first and second adjustable closed loops, the doubled repair loop may be rotated such that a location where the first and second adjustable closed loops are interlinked is at the tear in the tissue, and the first and second splice regions are generally remote from the location.

A closed tear in a tissue may be secured by self-cinching of a repair length of flexible strand in the first and second splice regions, respectively, of the flexible strand and tensioning the first and second free ends.

The flexible strand may be a single strand and the first and second splice regions thereof may be adjacent one another. The first and second splice regions may be spaced from one another by, for example, less than 6 mm and each of the first and second splice regions may have a shortened length of, for example, about 3 to about 6 mm.

DETAILED DESCRIPTION

This disclosure generally relates to a knotless surgical construct 10, 100 and method of tissue repair using the same, such as for repairing or closing torn soft tissue. For example, the surgical construct 10, 100 and method may be applied to an all-inside suture-based arthroscopic meniscal repair, in which a flexible strand or suture passes vertically or horizontally through or around the torn meniscus, and/or applied to closing a tear or torn area in soft tissue, such as a meniscus, thereby encircling the tear therein, without the need for fixation devices, such as anchors or implant, or without the need for knots, including arthroscopically or pre-tied knots. The knotless surgical construct 10, 100 and method are designed to simplify the repair while also reducing failures of the repair often resulting from the weakening of fixation knots, which loosens the repair. The knotless surgical construct 10, 100 and method may also allow multiple adjustments of the final tension state of the construct for a more flexible intraoperative handling, as well as achieving more reproducible tensioning around the tear of the damaged tissue. Flexible tensioning of the surgical construct 10, 100 enables the surgeon to standardize the construct security in the final step of the repair. A continuous compressive repair loop of the surgical construct disposed over a thickness of the tissue is designed to offer greater holding strength to the repair and maximize the load to failure in response to cyclic loading.

Referring to FIGS. 1-10, the surgical construct 10 generally comprises at least one flexible strand 12, such as a suture or the like, that is configured to encircle a tear 92 in the damaged soft tissue 90, e.g. a torn meniscus, by passing the flexible strand through or around the damaged tissue, thereby creating a continuous and adjustable repair loop 14, as seen in FIGS. 1 and 2A-2C. Final tensioning of the surgical construct 10 is achieved by shortening the repair loop 14 and by utilizing a self-locking device 20 to compress tissue, and fixation of the construct 10, without the use of any anchors, any implants or any knots, including pre-tied sliding knots or arthroscopically-tied knots.

Figure 2A:
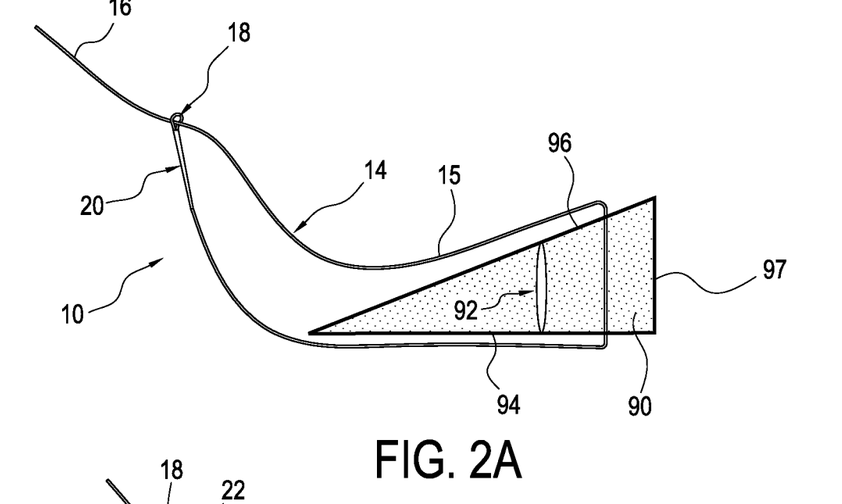
FIGS. 2A-2C are elevational views of the surgical construct illustrated in FIG. 1, showing the damaged tissue in cross-section.

The flexible strand 12 may comprise a free end 16 and a loop end 18 opposite the free end, to close the repair loop 14, with a repair length 15 of the strand 12 being defined between the ends 16 and 18, that creates the repair loop 14. The loop end 18 defines a loop at the most distal end of the strand 12 that is configured to receive the free end 16 of the strand 12, as seen in FIG. 2A. The self-locking device 20 may be positioned adjacent to the loop end 18 and is configured to engage the free end 16 of the strand 12 to lock the construct 10, thereby fixing the repair in place. Other mechanisms, besides the loop end 18, may be used to close the repair loop 14 and create a cinch at that point, such as a small suture tape portion, which may be pierced, for example.

The self-locking device 20 may be, for example, a friction based engagement device similar to a Chinese finger trap. In an embodiment, the self-locking device 20 is a finger-trap suture incorporated into or integral with the strand 12 through which the free end 16 extends. When tightening or pulling the self-locking device 20, the self-locking device lengthens and narrows such that the more the free end 16 is pulled, the more the circumference of device 20 shrinks around the strand 12 and the trap tightens, to fix the repair loop 14 once the repair loop is tensioned around the tear, without the use of any knots or fixation devices.

Figure 2B:
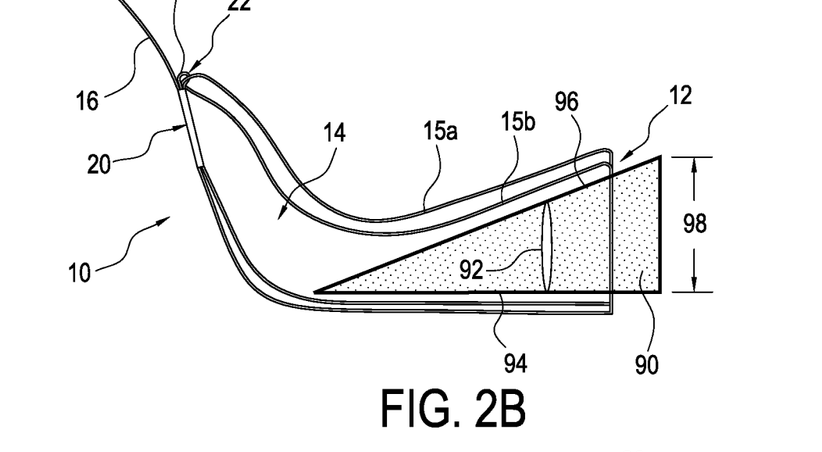
Figure 2C:
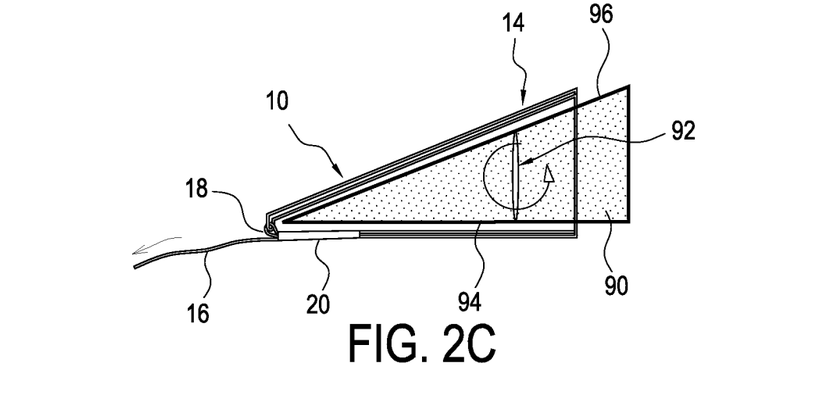

As seen in FIGS. 2A-2C, the surgical construct 10 is positioned to encircle the tear 92 rather than extend through the tear 92. The free end 16 of strand 12 initially extends in a direction through a first or inferior surface 94 of the tissue 90 near or adjacent to the tear 92, through a thickness 98 of the tissue 90 to exit a second or superior surface 96 of the tissue 90, which is opposite the first surface 94. Once the free end 16 exits the second surface 96 of the tissue 90, the free end 16 may be threaded through the loop end 18 of strand 12, as seen in FIG. 2A. This step of threading the free end 16 through the loop end 18 of strand 12 forms the initial continuous repair loop 14 around the tear 92, where the free end 16 extends through the loop end 18.

The repair loop 14 may then be doubled by reversing the direction of the free end 16, such that the repair loop 14 has at least two repair lengths 15a and 15b. That is, once the free end 16 is threaded through the loop end 18, the free end 16 may then be extended back through the second surface 96 of the tissue 90, back through the thickness of the tissue 90

(such as along the same path as when the free end 16 was first passed through the tissue), and back through the first surface 94 of the tissue 90, as seen in FIG. 2B. A cinch loop 22 is formed in the strand 12 that extends through and couples with the loop end 18 of the strand. After exiting the tissue's first surface 94, the free end 16 then extends through the self-locking device 20 near the loop end 18 of the strand 12. Pulling on the free end 16 of strand 12 then tightens the construct 10 to fix the repair loop 14 thereof around the tissue 90 and its tear 92, with the self-locking device 20 locking the construct 10 in place to secure the repair, without the need for anchors, knots, or the like, as seen in FIG. 2C. If needed, the construct 10 may be rotated around the tear 92, as shown in FIG. 2C.

A meniscus, for example, will have a generally triangular cross-sectional shape. The inferior surface 94 is the tibial surface, adjacent to the tibia, and the superior surface 96 is the femoral surface, adjacent to the femur, with an outer surface 97 extending therebetween. As seen in FIGS. 2A-2C, the strand's free end 16 of construct 10 exits from the tibial surface 94, and the strand's loop end 18 exits from the femoral surface 96. Although the repair is described as the free end 16 of strand first entering the inferior surface 94 of the tissue 90, the free end 16 may instead first enter the superior surface 96 of the tissue 90 to encircle the tear 92 in the same manner described above.

Figure 3A:
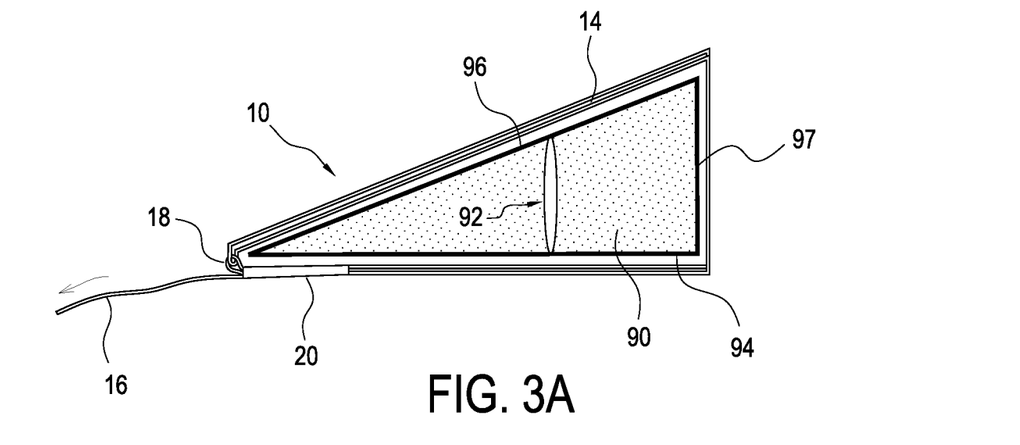
FIGS. 3A and 3B are elevational views of the surgical construct similar to FIGS. 2A-2C, showing the surgical construct locked after repair of the tissue.
Figure 3B:
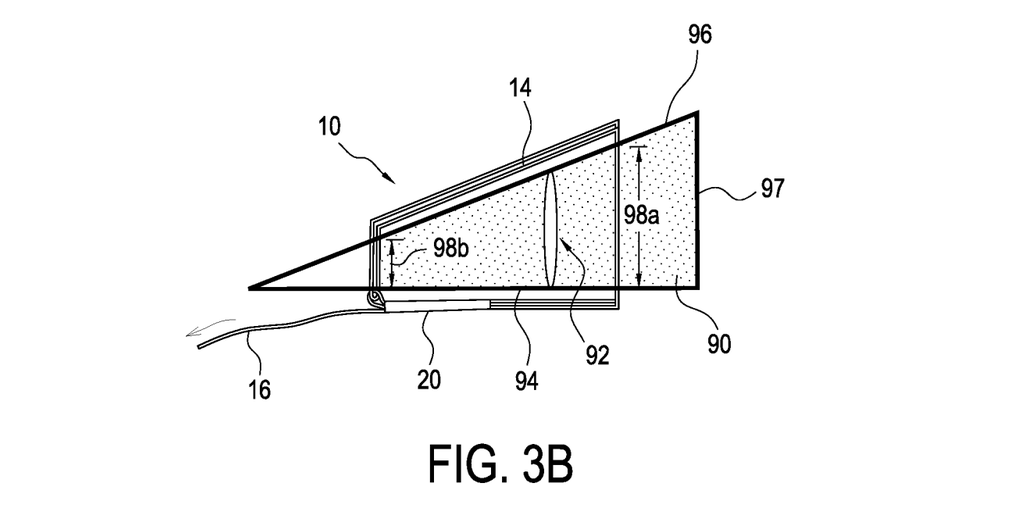

FIGS. 3A and 3B illustrate alternatives ways of encircling the tissue 90 and the tear 92 with the repair loop 14. For example, instead of extending the free end 16 of strand 12 through the thickness of the tissue 90, as described above, the repair loop 14 may be wrapped around the outside of the tissue, that is outside of surfaces 94, 96, and 97, as seen in FIG. 3A, without the free end 16 of strand 12 ever penetrating any surface of the tissue. Alternatively, the free end 16 of strand 12 may extend through the thickness of the tissue 90 at more than one place, such as on either side of the tear 92, like at thickness 98a and 98b, as seen in FIG. 3B. In this case, the free end 16 of strand 12 enters and exits each of the first and second surfaces 94 and 96 twice and both the free end 16 and the loop end 18 exit the tissue from the same side or surface, such as interior surface 94.

Figure 1:
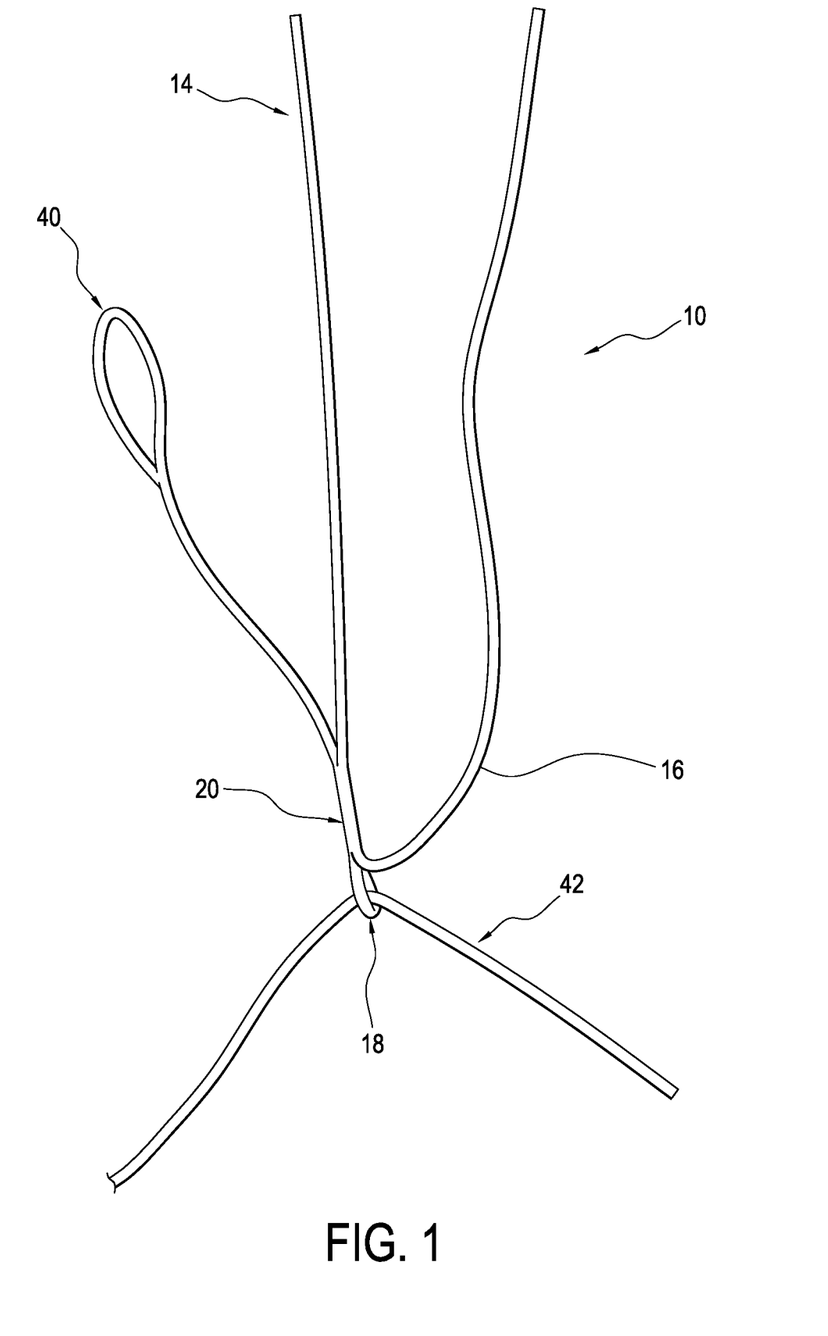
FIG. 1 is a view of an exemplary knotless surgical construct.
Figure 4:
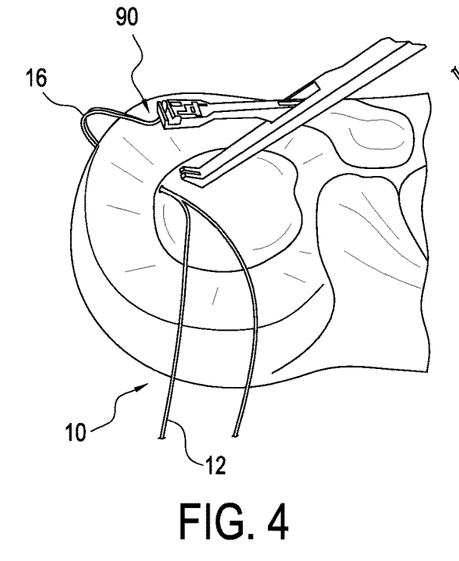
FIGS. 4-10 illustrate exemplary method steps for repairing damaged tissue using the knotless surgical construct illustrated in FIG. 1.
Figure 5:
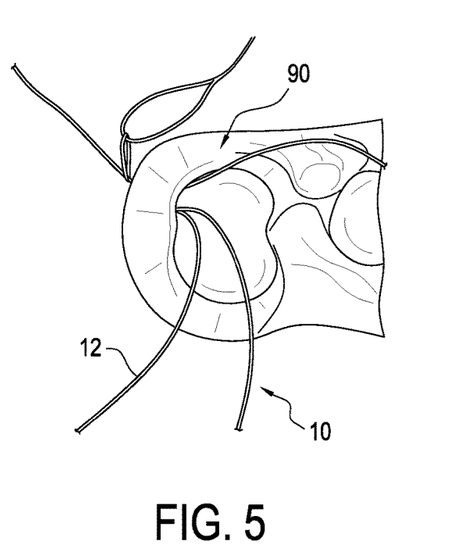
Figure 6:
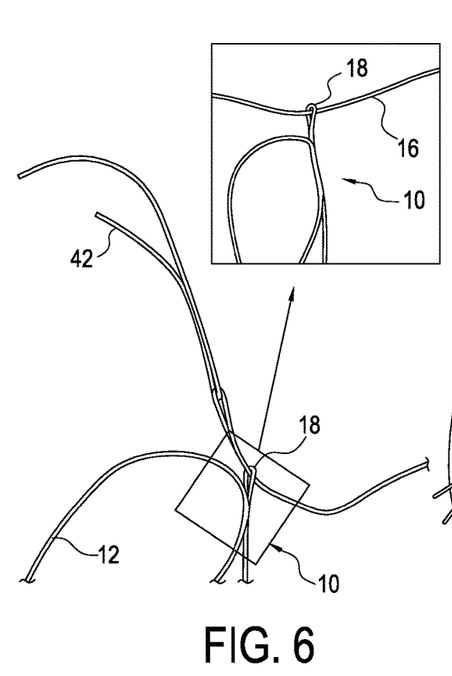
Figure 7:
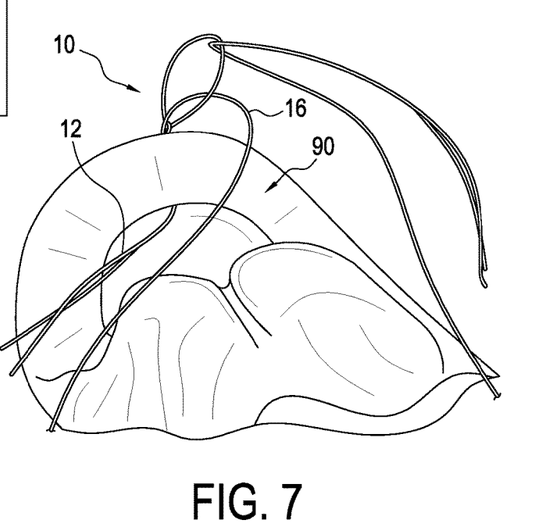
Figure 8:
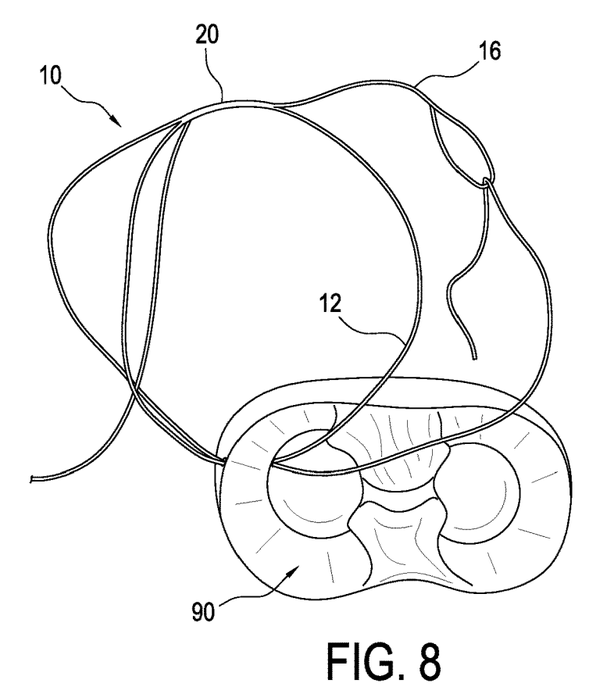
Figure 9:
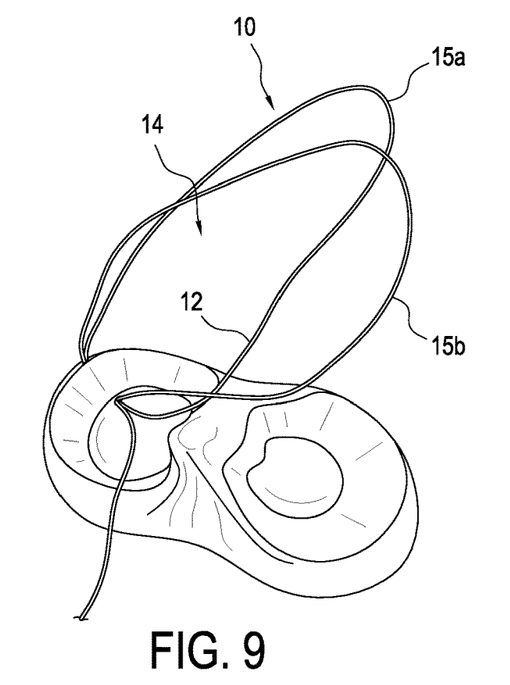
Figure 10:
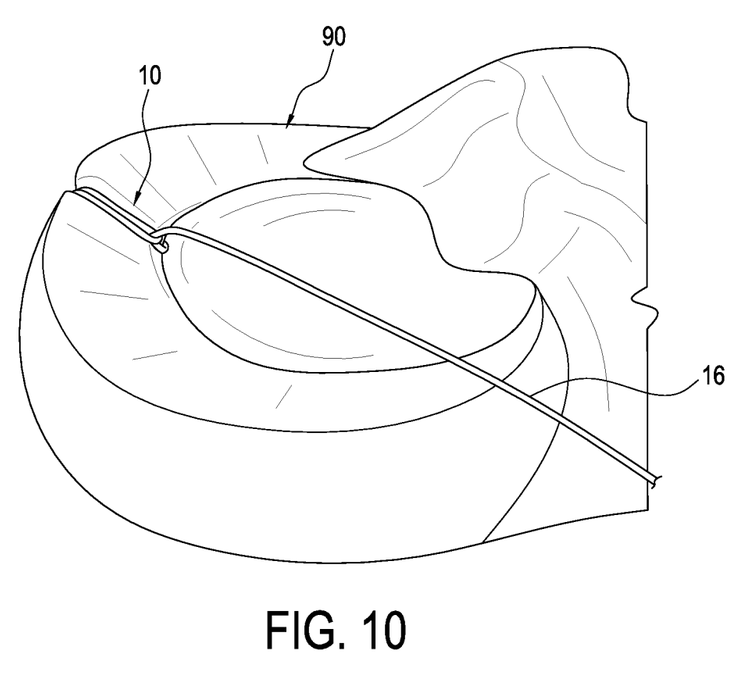

FIGS. 4-10 illustrate an exemplary method of tissue repair, for example a torn meniscus 90, using the surgical construct 10. Initially, the free end 16 of strand is extended through a thickness of the meniscus using a shuttling device 40, as seen in FIGS. 1 and 4. The shuttling device 40, may be, for example, a shuttle suture incorporated into or integral with the free end 16 of strand 12. The repair length of the strand 12 is then passed through the meniscus, as seen in FIG. 5. The strand's free end 16 is then passed through the loop end 18, as seen in FIG. 6. Another shuttling device 42 may be used to facilitate threading of the free end 16 through the loop end 18. The free end 16 and repair length of strand 12 may then be passed backward through the meniscus, as seen in FIG. 7. The strand's free end 16 is then passed through the finger-trap suture 20, as seen in FIG. 8, thereby forming the continuous repair loop 14 with double the strand repair lengths, as seen in FIG. 9. The construct 10 may then be tightened by pulling on the strand's free end 16, to shrink the repair loop, compress the tissue 90, and fix the construct 10 in place, by self-locking, thereby securing the repair, as seen in FIG. 10.

Referring to FIGS. 11-18, the surgical construct 100 generally comprises a flexible strand 102, such as a suture or the like, that is configured to close a tear 192 in damaged soft tissue 190 by passing it through or around the damaged tissue and creating a doubled repair loop 104 (FIG. 17) this is adjustable, using a passer 106 loaded on the flexible strand 102. Final tensioning of the surgical construct 100 is achieved by shortening or decreasing the perimeter of the repair loop 104 to compress the soft tissue and securing the closure of the construct 100 (FIG. 18), without the use of any anchors or fixation devices, any implants, or any knots, including pre-tied sliding knots or arthroscopically-tied knots.

Figure 11:
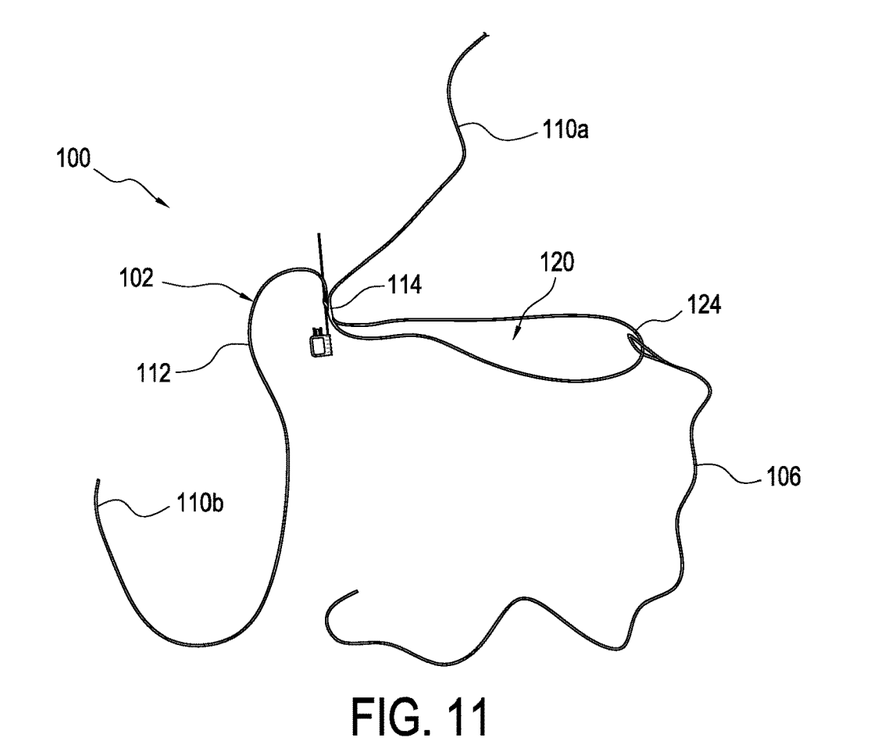
FIG. 11 is a view of another exemplary knotless surgical construct.
Figure 12:
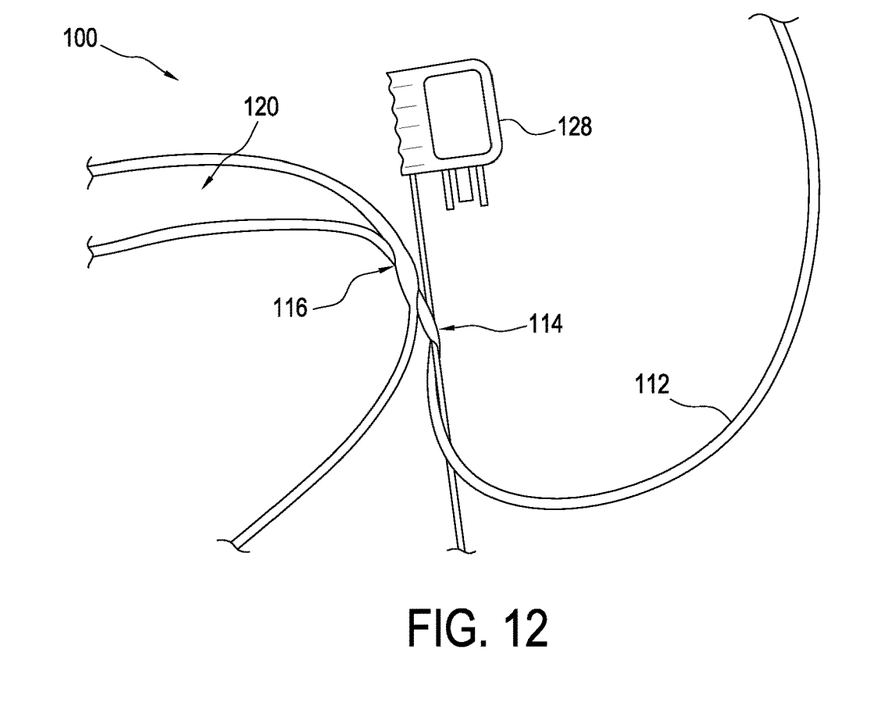
FIG. 12 is an enlarged partial view of the knotless surgical construct illustrated in FIG. 11.

The flexible strand 102 may be a single strand, such as a single suture, that comprises opposite first and second free ends 110a and 110b, and a repair length 112 therebetween, as seen in FIGS. 11 and 12. The repair length 112 may have first and second splice regions 114 and 116. The design of the construct 100 and method of use allows for the splice regions 114 and 116 in the repair length 112 to be both shorter in length and closer to one another than in conventional constructs. For example, the splice regions 114 and 116 can be adjacent one another, that is the splice regions can be located next to one another with a reduced or small space therebetween. In an embodiment, the space between the first and second splice regions 114 and 116 is less than 6 mm, and may be about 2 mm to 5 mm. And each splice region 114 and 116 can also have a shortened length that may be about 3 mm to 6 mm.

The surgical construct 100 and method of use can form first and second adjustable closed loops 120 and 122 via the first and second splice regions 114 and 116, respectively, in the flexible strand 102. The adjustable closed loops 120 and 122 can interlink with one another to form the doubled repair loop 104. The adjustable closed loops 120 and 122 may be interlinked at a location 115 generally opposite from the first and second splice regions 114 and 116, such as at the loops ends 124 and 126 of the first and second loops 120 and 122, respectively. The doubled repair loop 104 being made up of two loops, i.e. the adjustable closed loops 120 and 122, provides reinforcement and strength to the repair loop 104, and thus the tissue repair, while using only a single strand, i.e. flexible strand 102. And no fixation devices, such as buttons and the like, are needed to close the torn tissue using the construct 100. As such, the flexible strand 102 is devoid of any fixation devices. The first and second adjustable loops 114 and 116 are tensionable by pulling the first and second free ends 110a and 110b, respectively, to reduce the doubled repair loop 104 and close the tear in the tissue without the use of any knots or fixation devices.

Figure 13:
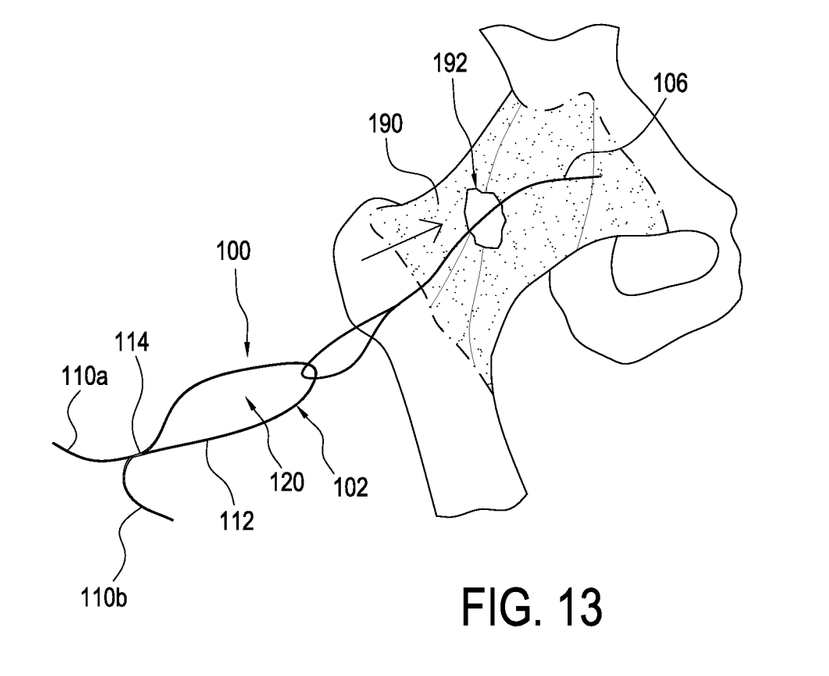
FIGS. 13-18 illustrate exemplary method steps for repairing damaged tissue using the knotless surgical construct illustrated in FIG. 11.
Figure 14:
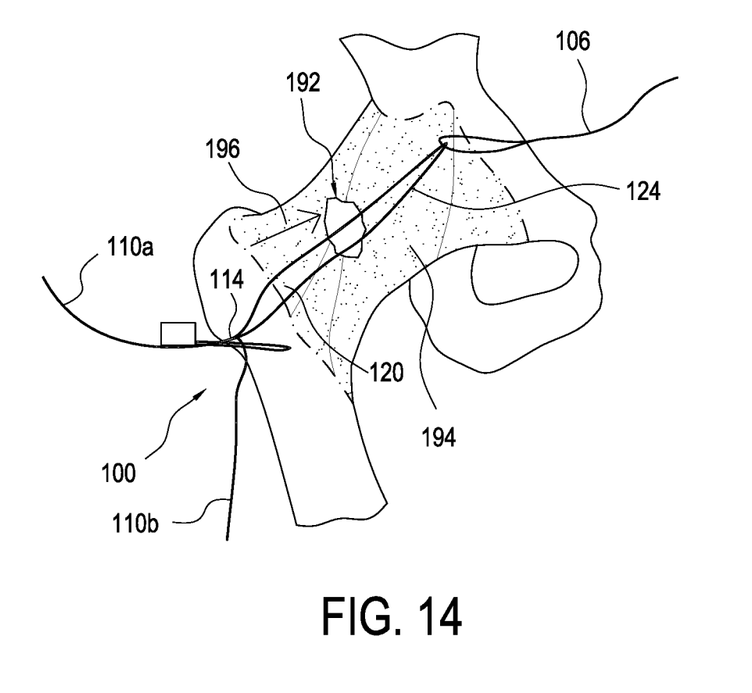

FIGS. 13-18 illustrate an exemplary method of tissue repair, for example a torn hip capsule 190, using the surgical construct 100. Initially, the first free end 110a of the flexible strand 112 may be threaded through the first splice region 114 to create the first adjustable closed loop 120, as seen in FIG. 13, using any known threading device, such as a needle 128. Next, the first adjustable closed loop 120 may be passed through the tear 192 in the tissue 190 using the passer 106 which may be coupled to the loop 120. The passer 106 may be any known passer or shuttle device, such as a wire. The first adjustable closed loop 120 is passed through the tear 192 such that it spans the tear 192, that is its loop end 124 is located at one side 194 of the tear 192 and the first splice region 114 is located at the other side 196 of the tear, as seen in FIG. 14.

Figure 15:
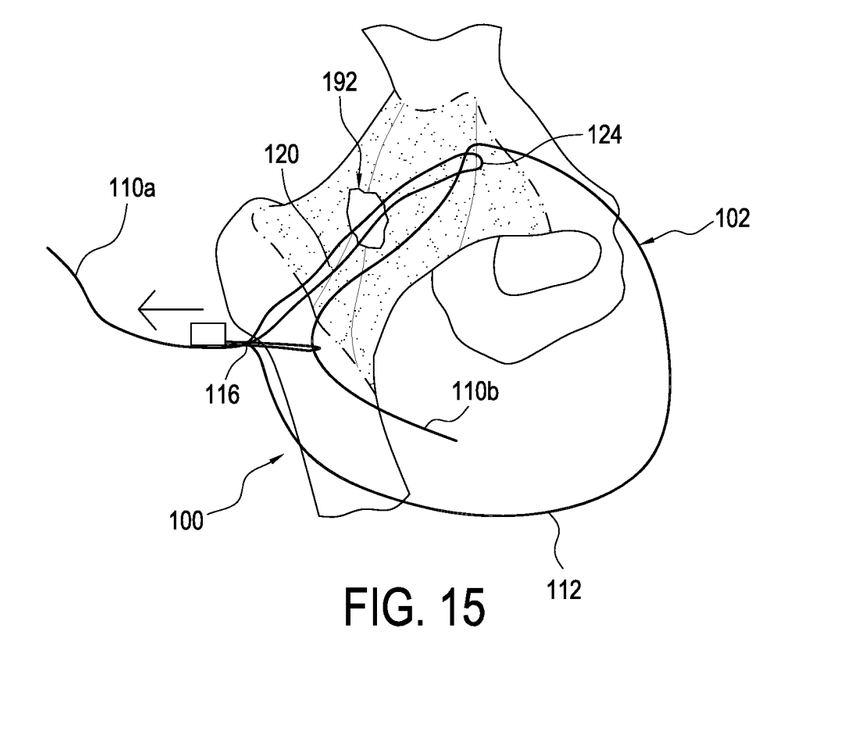
Figure 16:
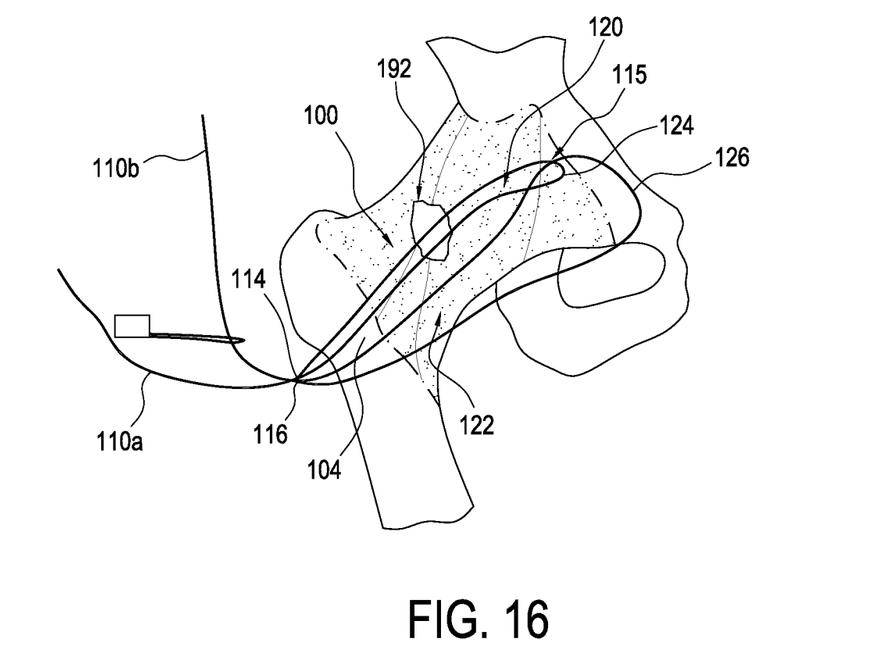

Once the first adjustable closed loop 120 is passed through the tear 192, the second free end 110b of the flexible strand 102 is can be passed through the loop end 124 of the first adjustable closed loop 120 using another passer or the same passer 106, as seen in FIG. 15. The second free end 110b can then be threaded through the second splice region 116 in the flexible strand 102 to create the second adjustable closed loop 122 such that it is interlinked with the first adjustable closed loop 120 at, for example, their loops ends 124 and 126. The interlinked first and second adjustable closed loops 120 and 122 form the adjustable doubled repair loop 104, as seen in FIG. 16.

Figure 17:
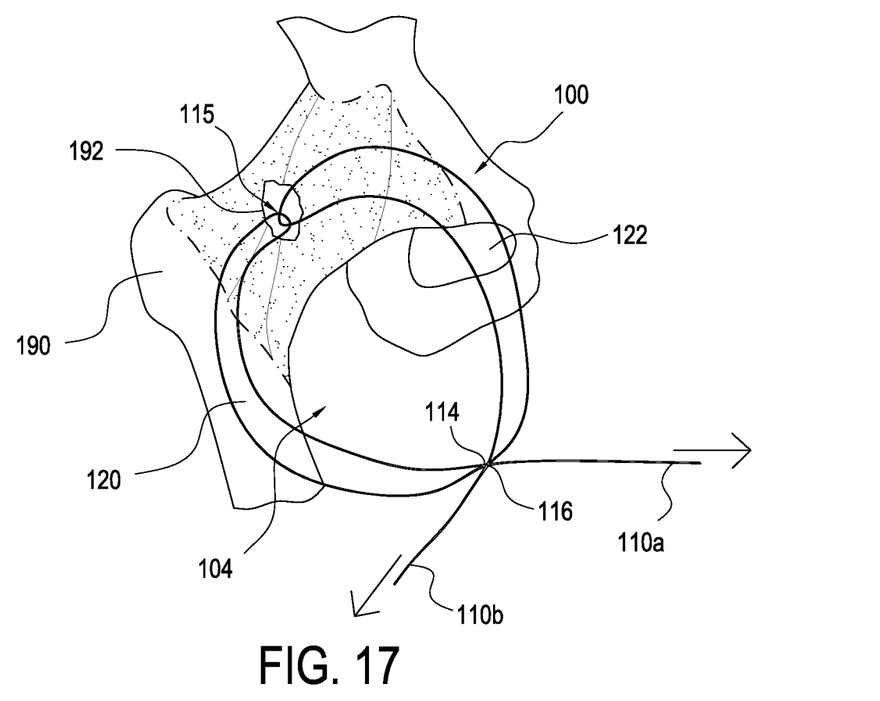
Figure 18:
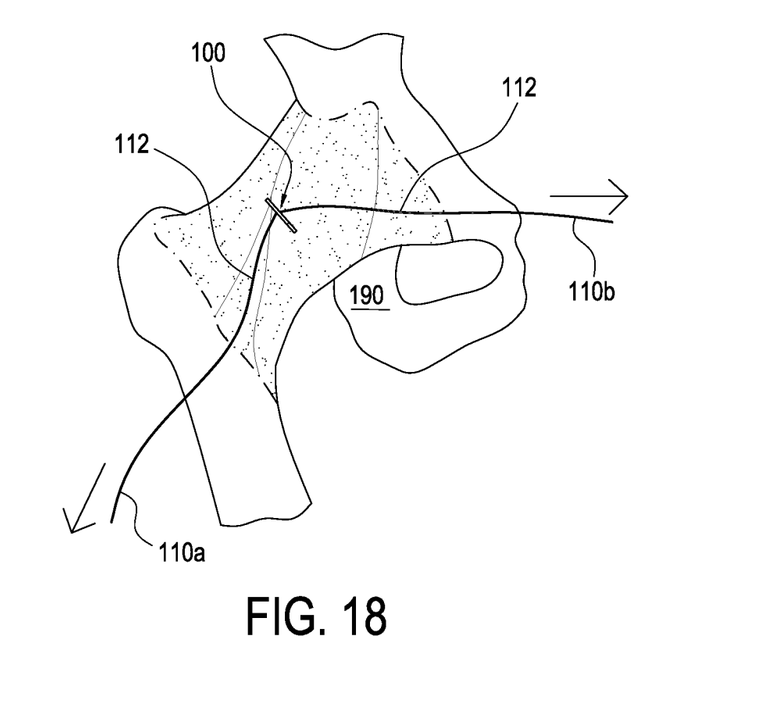

After the doubled repair loop 104 is formed, the first and second free ends 110a and 110b of the flexible strand 102 may be pulled, as seen in FIG. 17, to decrease the perimeters of each of the first and second adjustable closed loops 120 and 122, respectively, and thereby decreasing or reducing the perimeter of the doubled repair loop 104 until the tear in the tissue is closed without the use of knots or fixation devices, as seen in FIG. 18. The construct 100 may be self-cinching due to the repair length 112 of the flexible strand 102 extending through the splice regions 114 and 116 and the tensioning of the construct via the strand's first and second free ends 110a and 110b, to secure the repair and keep the torn tissue closed.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A method of knotless tissue repair, the method comprising:

threading a first free end of a flexible strand of a knotless surgical construct through a first splice region in the flexible strand to create a first adjustable closed loop;

passing the first adjustable closed loop through a tear in tissue such that a loop end of the first adjustable closed loop is located at one side of the tear and the first splice region is located at the other side of the tear;

passing a second free end of the flexible strand through the loop end of the first adjustable closed loop and threading the second free end through a second splice region in the flexible strand to create a second adjustable closed loop that is interlinked with the first adjustable closed loop such that the first and second adjustable closed loops form a doubled repair loop that is adjustable; and pulling the first and second free ends of the flexible strand to decrease the perimeters of the first and second adjustable closed loops, respectively, thereby decreasing the perimeter of the doubled repair loop, until the tear in the tissue is closed without the use of knots or fixation devices.

2. The method of claim 1, wherein a passer is coupled to the loop end of the first adjustable closed loop to pass the first adjustable closed loop through the tear.

3. The method of claim 2, wherein the passer is decoupled after the first adjustable closed loop is passed through the tear.

4. The method of claim 1, wherein a passer is coupled to the second free end of the flexible strand to pass the second free end through the loop end of the first adjustable closed loop.

5. The method of claim 1, further comprising, before pulling the first and second free ends of the flexible strand to decrease the perimeters of the first and second adjustable closed loops, rotating the doubled repair loop such that a location where the first and second adjustable closed loops are interlinked is at the tear in the tissue, and the first and second splice regions are generally remote from the location where the first and second adjustable closed loops are interlinked.

6. The method of claim 1, wherein the flexible strand is a single strand and the first and second splice regions are adjacent one another.

* * * * *